United States Patent [19]

Bonn

[11] Patent Number: 5,097,842
[45] Date of Patent: Mar. 24, 1992

[54] DEVICE FOR WITHDRAWING FLUIDS

[76] Inventor: Gina B. Bonn, 7476 Stacy Dr., Nashville, Tenn. 37221

[21] Appl. No.: 557,408

[22] Filed: Jul. 23, 1990

[51] Int. Cl.$^5$ .............................................. A61B 5/02
[52] U.S. Cl. ...................................... 128/762; 604/33
[58] Field of Search ................ 604/33, 249, 191, 187; 128/762, 763, 765, 766; 137/625.48, 883; 251/325

[56] References Cited

U.S. PATENT DOCUMENTS

| | | | |
|---|---|---|---|
| 3,405,706 | 10/1968 | Cinqualbre | 128/762 |
| 3,494,351 | 2/1970 | Horn | 128/762 |
| 3,696,806 | 10/1972 | Sausse | 604/191 X |
| 3,859,985 | 1/1975 | Eckhart | 604/33 X |
| 4,676,256 | 6/1987 | Golden | 128/762 |
| 4,680,026 | 7/1987 | Weightman et al. | 604/33 |
| 4,843,017 | 6/1989 | Oberhardt et al. | 128/762 X |

FOREIGN PATENT DOCUMENTS 2249119  4/1973  Fed. Rep. of Germany ...... 128/762

OTHER PUBLICATIONS

Copy of one page of a brochure entitled "Blood Collection".
Copy of a brochure entitled "What You Should Know About Vacutainer Brand Blood and Blood/Urine Collection Kits . . .".
Copy of a Certificate of Manufacturer Label for the 4990 Kit Manufactured by Becton Dickinson.
Copy of one page of instructions entitled "Instructions for Use—Vacutainer Brand Blood Collection System".

Primary Examiner—Max Hindenburg
Attorney, Agent, or Firm—Kilpatrick & Cody

[57] ABSTRACT

Devices for extracting blood or other body fluids, and particularly for extracting blood from the umbilical cord. A hypodermic needle for insertion into the umbilical cord is attached to a valve housing, to which is connected one or more vacuum containers or test tubes. One or more valves in the housing may be positioned to connect the needle with each vacuum container or test tube as desired. Bodily fluids may thus be extracted without the need to perform multiple injections or to stick multiple vacuum containers with the same syringe. The devices lend convenience to the newborn blood testing process and reduce the chances of inadvertent blood spillage.

7 Claims, 5 Drawing Sheets

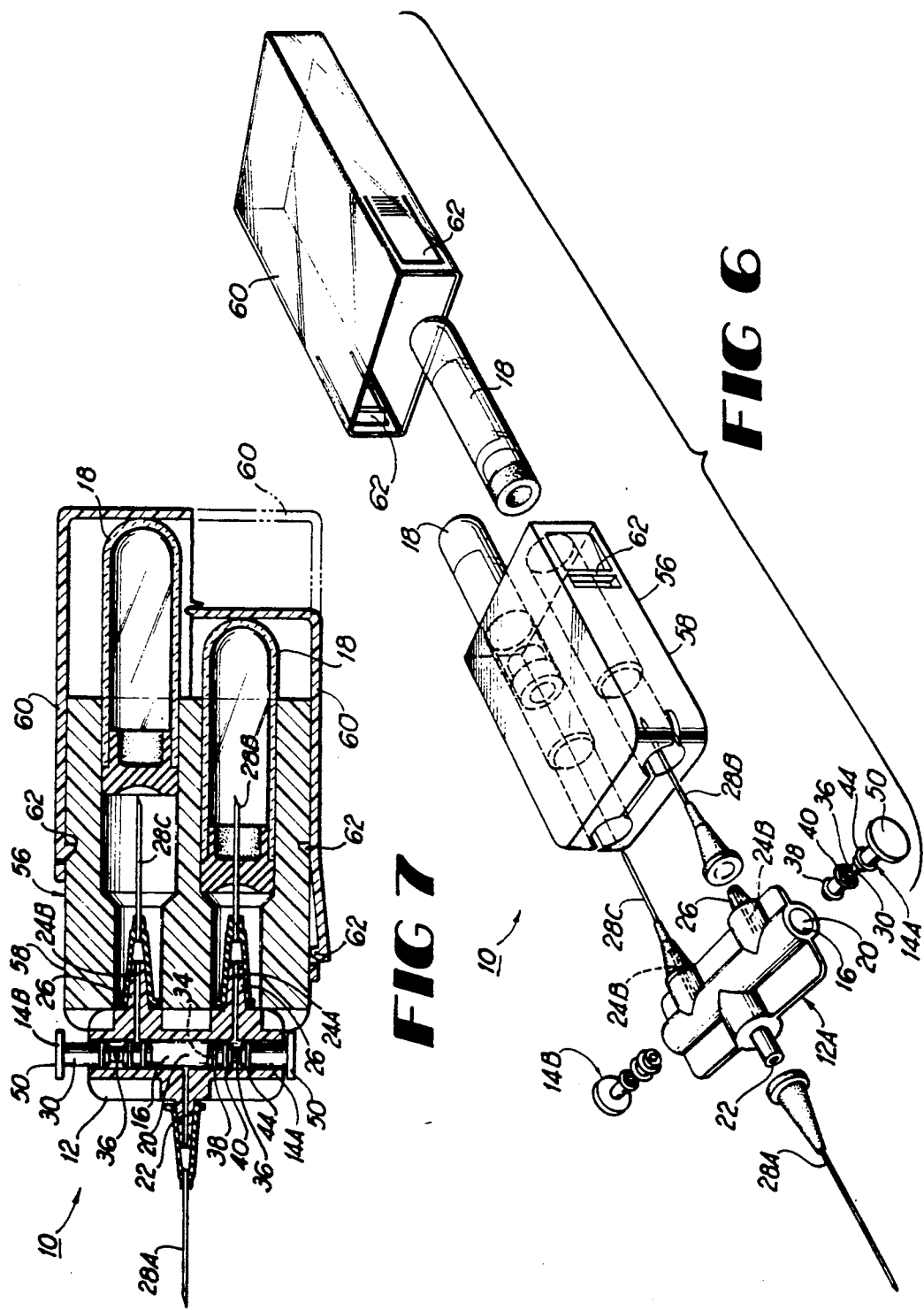

DEVICE FOR WITHDRAWING FLUIDS

This invention relates to devices for obtaining blood and other body fluids from humans and animals. The invention is particularly well suited for taking blood from the human umbilical cord.

BACKGROUND OF THE INVENTION

Laws and health regulations of most states require that blood samples be taken from newborn babies shortly after birth. Such blood tests are used for blood typing, screening for certain blood dyscrasias, toxicological studies and other purposes. Frequently, two blood samples in two separate tubes are required. One sample is typically obtained in a "clot" tube without any added chemical; the other is usually obtained in an anticoagulation tube which also contains a predetermined amount of an anticoagulant such as ethylene diamine tetra acetic acid (EDTA).

Previous techniques for extracting blood from umbilical cords have included simply dripping blood from the end of an umbilical cord into two separate open end test tubes or vacuum test tubes or containers, such as those known as VACUTAINER brand containers, from which the rubber stoppers have been removed. (VACUTAINER is a registered mark of Becton Dickinson and Company, of Rutherford, N.J.) Other techniques involve drawing blood from the umbilical cord using a standard hypodermic needle and syringe, and then sticking the needle through the rubber stoppers of two separate vacuum containers serially to insert the blood. Both methods allow spillage of blood in the delivery room and elsewhere, with the obvious possibility of contamination of the area and the attending staff. With the recent increased danger of AIDS and other blood-borne diseases, the risks presented by such spillage and contamination have increased dramatically.

SUMMARY OF THE INVENTION

The present invention allows extraction of blood and other bodily fluids using a single needle to supply two or more vacuum container or test tube samples. The hypodermic needle which is used for insertion into the body is attached to a valve housing which in turn supplies a number of vacuum containers or test tubes. One or more valves in the housing may be positioned to connect the insertion needle with each vacuum container or test tube as desired. Bodily fluids may thus be extracted without the need to perform multiple body insertions or to fill multiple vacuum containers with a syringe.

It is therefore an object of the present invention to provide a body fluid extraction device which allows body fluids to be withdrawn more safely and efficiently.

It is an additional object of the present invention to provide a low cost, efficient blood extraction device which allows two or more vacuum container or test tube samples to be withdrawn using a single insertion into the body.

Other objects, features and advantages of the present invention will become apparent with reference to the remainder of this document.

BRIEF DESCRIPTION OF THE DRAWINGS

FIG. 6 is an exploded perspective view of a fifth embodiment of the present invention which includes a vacuum container enclosure attached to the valve housing.

FIG. 7 is a cross-sectional view of the device of FIG. 6.

DETAILED DESCRIPTION OF THE DRAWINGS

Figure 1:
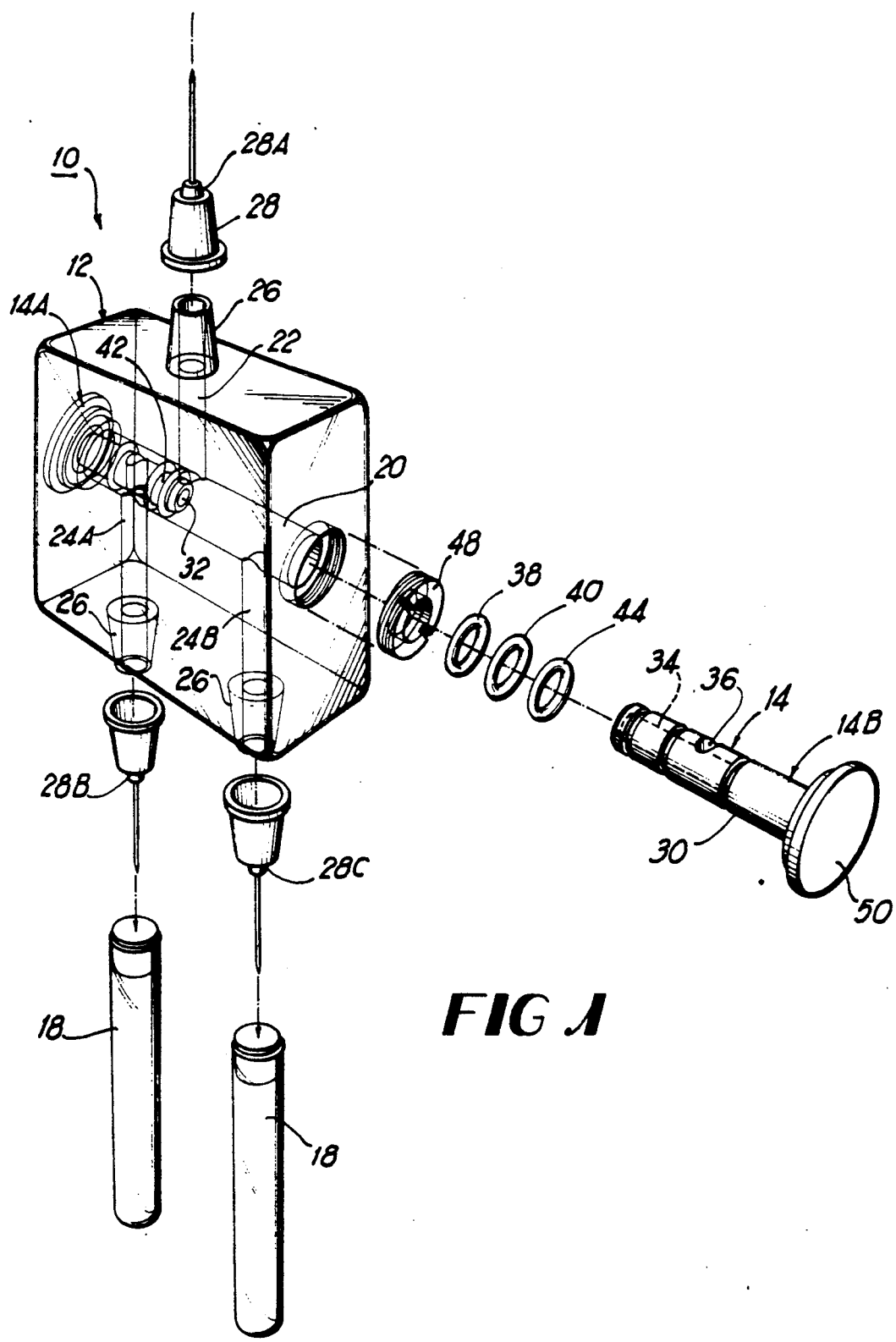
FIG. 1 is a perspective, partially exploded view of a first embodiment of a device according to the present invention.

FIG. 1 shows an exploded perspective view of a device 10 according to a first embodiment of the present invention. Device 10 includes a valve housing 12 that cooperates with valves 14 to connect chambers 16 in the housing 12 together in order to route blood or other body fluids to the desired test tube, vacuum container or other sample holder 18.

In greater detail, the device 10 of FIG. 1 includes a housing 12 which may be formed of injection molded plastic material or otherwise formed as desired of appropriate materials. Chambers 16 may be formed during the molding process or later, by machining or as otherwise desired. A central chamber 20, in which portions of the valves 14 are disposed, communicates with an intake chamber 22 and one or more exhaust chambers 24. The intake chambers 22 and exhaust chambers 24 penetrate opposite sides of housing 12 in the illustrated embodiment; they may however, extend in any desired direction and penetrate any surface of the housing 12. Similarly, housing 12 may be of any desired shape and configuration to accommodate chambers 16.

Shoulders or other appropriate accommodations 26 may be formed on, formed into or otherwise made part of the exterior surface of housing 12 to receive conventional lure-lok type or other desired needles 28. The intake chamber 22 communicates with an insertion needle 28A which is intended for insertion into the umbilical cord or other body part. Exhaust or vacuum container needles 28B and 28C are attached to the accommodations 26 that surround exhaust chambers 24. Other components, such as resilient accommodations 26 which take the place of vacuum container stoppers, may be used in place of needles 28B and 28C to allow exhaust chambers 24 to communicate with the interiors of the vacuum containers 18 without the need for needles. Similarly, the insertion needle 28A and/or exhaust needles 28B and 28C may be connected integrally to housing 12 by having the housing 12 molded around the needles, or as otherwise desired, and they need not be lure-lok-type needles.

Figure 2:
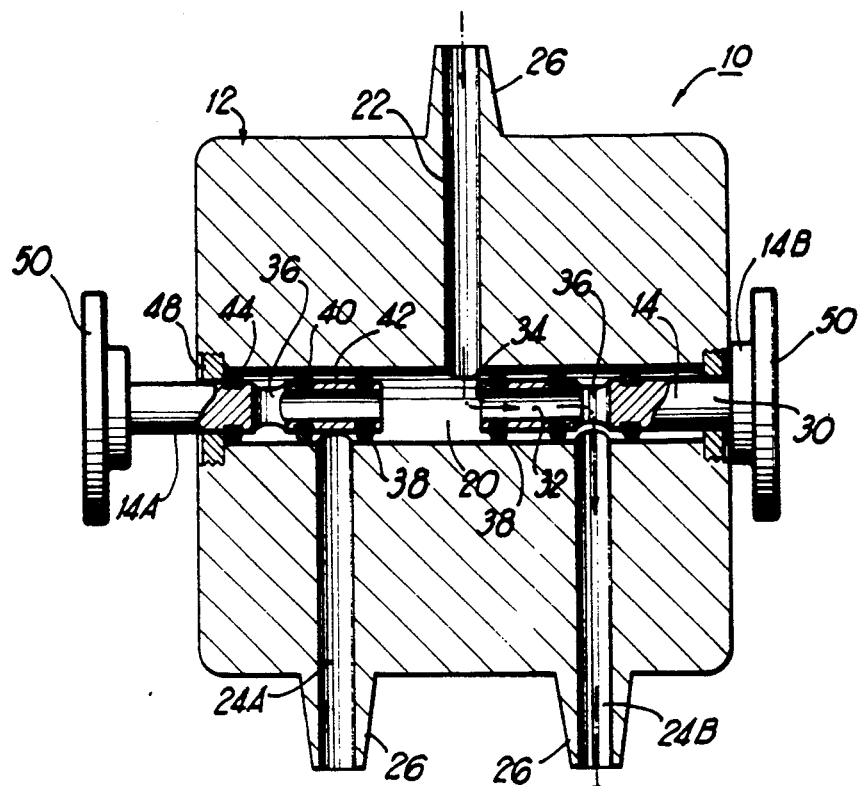
FIG. 2 is a cross-sectional view of a portion of the device of FIG. 1 when assembled.

Operation of valves 14 may perhaps be better understood with reference to FIG. 2, in addition to FIG. 1. The device of FIGS. 1 and 2 includes two valves 14A and 14B, each of which valves includes a shaft 30 that slides generally within central chamber 20. FIG. 2 shows left-hand valve 14A closing off the left exhaust chamber 24A, while the right-hand valve 14B allows blood to flow between the intake chamber 22 and the right exhaust chamber 24B.

In the devices shown in FIGS. 1 and 2, the valve shafts 30 include a hollow portion 32 which opens at two ports along the shaft: a first port 34 and a second port 36. Ports 34 and 36 are spaced apart from one another along the length of shaft 30 in the embodiments shown in FIGS. 1 and 2. First port 34 is located on the end of shaft 30 in the valves 14 of FIGS. 1 and 2, while first port 34 opens onto the sides of the valve shafts 30 in the embodiment shown in FIGS. 3 and 3A-B. In either event, a sealing means 38 is placed on the shaft 30 between first and second ports 34 and 36 to prevent flow of fluid between intake chamber 22 and exhaust chambers 24 except when a valve 14 is in the "open" position (the position that allows flow of fluid through that valve between the intake chamber 22 and exhaust chamber 24). In the embodiment shown in FIGS. 1-3, the sealing means 38 comprises a pair of o-rings 40 which form a closed space 42 defined by the o-rings 40, the central chamber 20 surface and the valve shaft 30.

Figure 3:
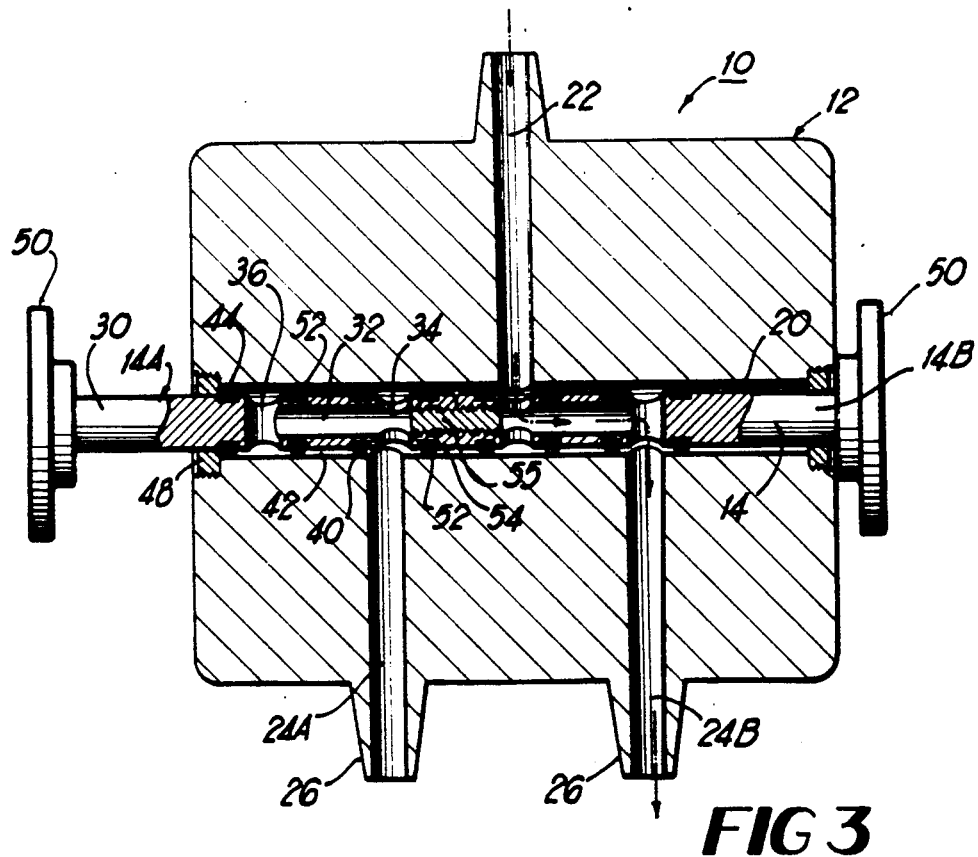
FIG. 3 is a cross-sectional view of a second embodiment of a device according to the present invention.

Each valve shown in the embodiment shown in FIGS. 1-3 also includes an outer sealing means 44 which prevents fluid from escaping the valve housing 12 through the central chamber 20. The outer sealing means 44 may also be an o-ring or any other desired structure. Outer sealing means 44 in the embodiments shown in FIGS. 1-3 also cooperates with a retainer 48 to prevent valve 14 from being retracted outside of the valve housing 12 beyond the "closed" position (the position where the valve 14 closes off communication to exhaust chamber 24). The retainer 48 also centers valve shaft 30 in central chamber 20, together with the assistance of o-rings 40 and 46. Retainer 48 is threaded or otherwise retained in housing 12.

Each valve shaft 30 may be capped with a button 50 or other comfortable grip, knob or positioning device to allow valve 14 to be moved to the open and closed positions as desired.

Figure 3A:
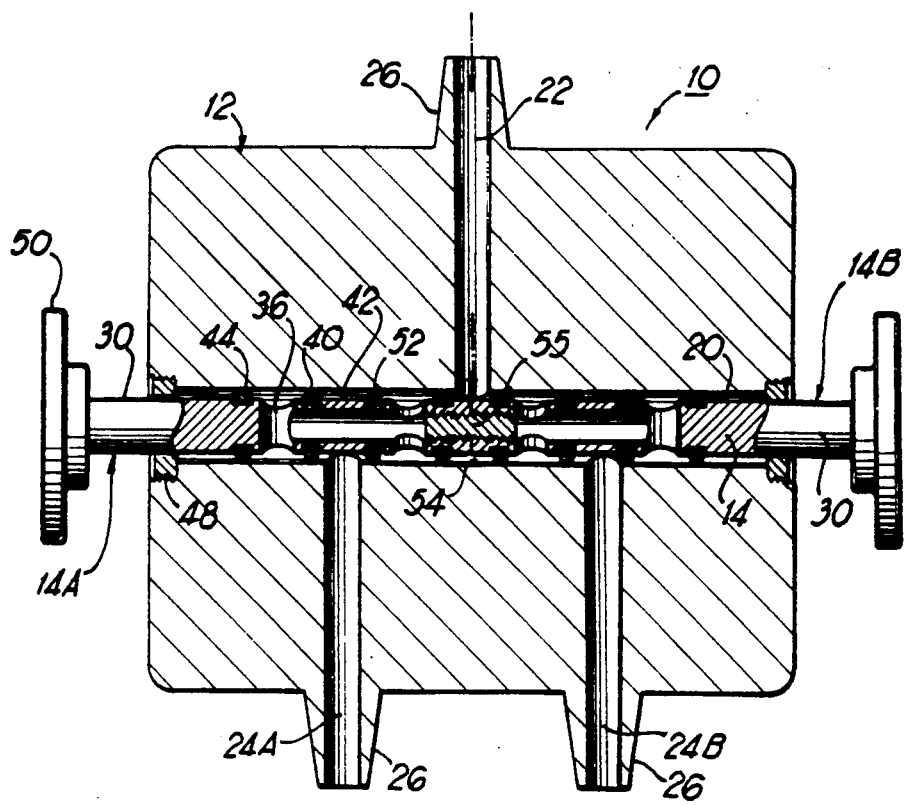
FIGS. 3A and 3B are cross-sectional views of the device of FIG. 3 showing the valves in differing positions.
Figure 3B:
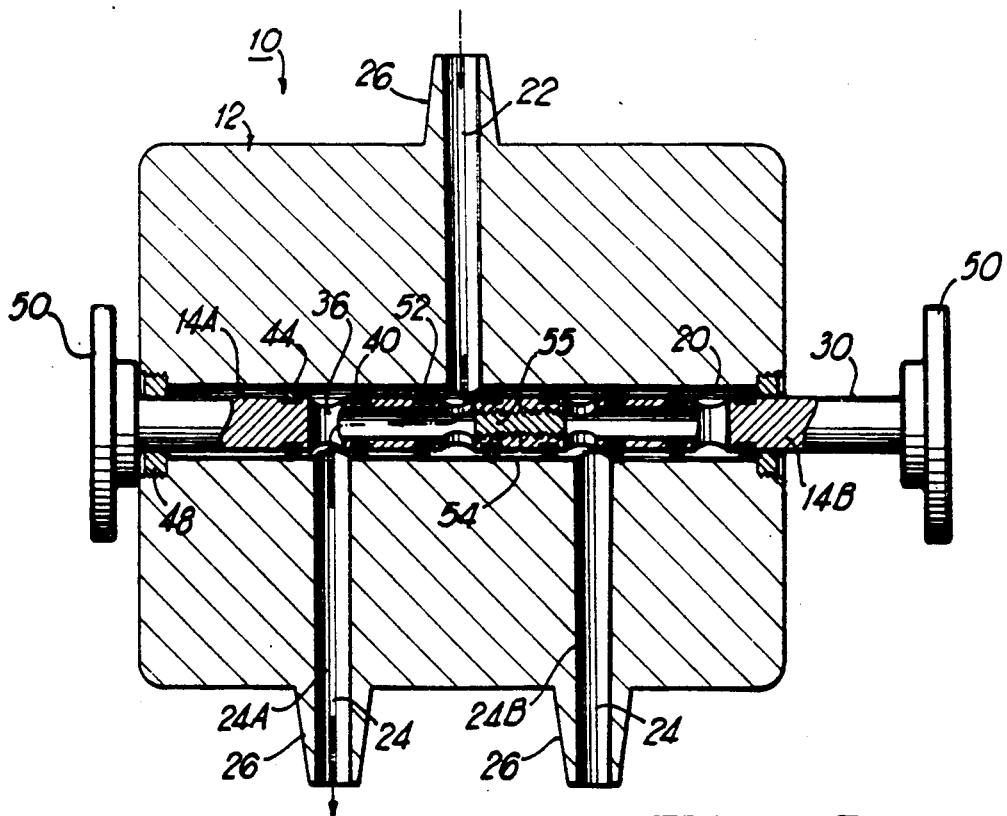

The valve shown in FIGS. 3 and 3A-B cooperates with its adjacent valve 14 to close off one exhaust chamber 24 as the other is opened, and vice versa. This effect is accomplished through spacing of first and second ports 34 and 36, together with o-rings 40. Such structure requires an additional set of sealing means or o-rings 52 on each shaft placed beyond first port 34 from second port 36, in order to prevent fluid from flowing simultaneously to both first ports 34 when either valve is open. These two sealing means 52 also form an additional closed space 54 which, similar to the manner of closed spaces 42, seals off intake chamber 22 when both valves are in the closed position. A plug 55 may be threaded or otherwise formed or fitted into the valve shafts 30 in order to close off their ends, and, if desired, to connect the two shafts so that retracting one valve 14 from the housing 12 draws the other into the housing.

In operation, as shown in FIG. 2, left-hand valve 14A is in the closed position so that its closed space 42 seals off left exhaust chamber 24A. Right-hand valve 14B is pushed in to the open position, so that the closed space 42 slides between the places where central chamber 20 meets intake chamber 22 and right exhaust chamber 24B. Fluid is allowed to flow from intake chamber 22 into central chamber 20, into first port 34 of valve 14B, through hollow portion 32, out second port 36 and into exhaust chamber 24B. It is prevented from flowing out central chamber 20 by outer sealing means 44. When the desired vacuum container has been filled, valve 14 may be pulled to the closed position and, if desired, left-hand valve 14A may be pushed to the open position.

Figure 4:
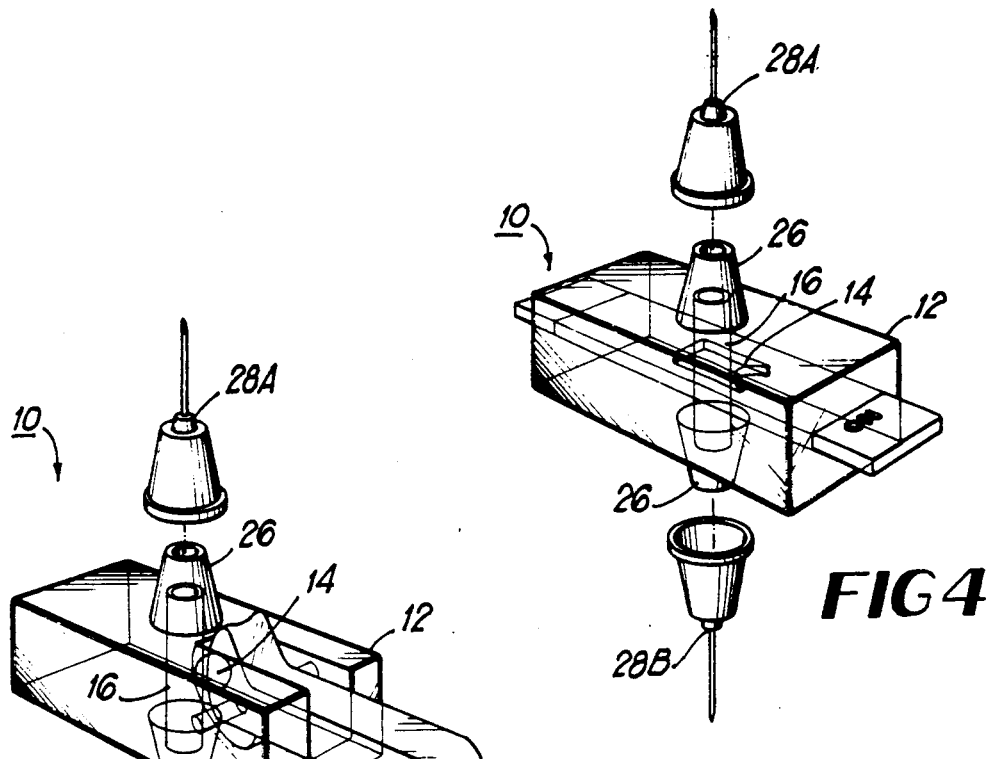
FIG. 4 is perspective view of a device according to a third embodiment of the present invention.
Figure 5:
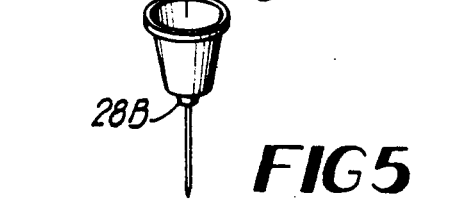
FIG. 5 is perspective view of a device according to a fourth embodiment of the present invention.
Figure 5A:
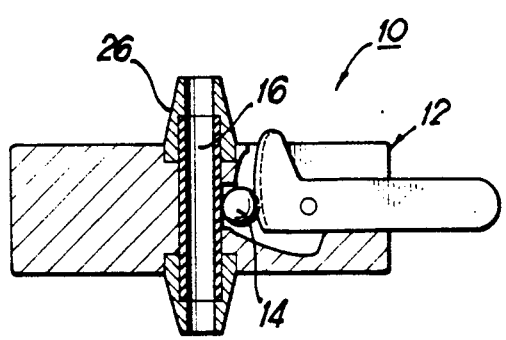
FIGS. 5A and 5B are cross-sectional views of a portion of the device of FIG. 5 showing the valve in differing positions.
Figure 5B:
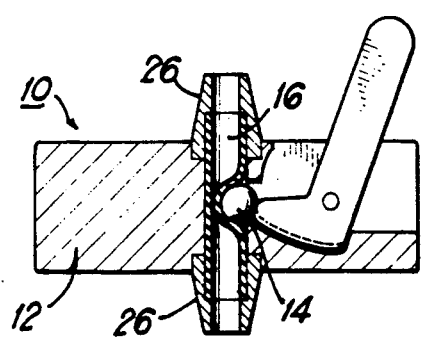

Valves 14A and 14B as shown in FIGS. 1 and 2 may be used to allow both vacuum containers to be filled simultaneously, and to close both off simultaneously, or to allow the vacuum containers to be filled serially. Accordingly, the invention specifically contemplates the intake chamber 22 being connected simultaneously or serially to any one or a combination of exhaust chambers 24. Indeed, no central chamber 20 is necessary, nor are the relatively complex valve structures shown in FIGS. 1-3. The invention may just as easily be accomplished by any other desired structure, including using a flexible, y-shaped chamber which connects the insertion needle 28A and the vacuum containers, the legs of which Y may be pinched off to prevent flow of fluid. FIG. 4 shows a sliding plate which pinches such a flexible chamber in a single vacuum container device. FIGS. 5, 5A and 5B show a ball and biasing lever which also pinches off a flexible chamber, and these principles can easily be applied to a device 10 which supports two vacuum containers.

FIGS. 6 and 7 show a perspective and a cross-sectional view, respectively, of a fifth embodiment of an extractor 10 according to the present invention. This version includes an enclosure 56 which surrounds the vacuum containers, and a valve housing 12 which mates with the enclosure 56. More specifically, enclosure 56 is preferably formed of two elements, a first element 58 which mates with the valve housing 12A and a second element 60 which cooperates with first element 58 in a sliding relationship not only to house the vacuum containers 18 but also to press them into place on exhaust needles 28B and 28C. This version can therefore accommodate a "clot" vacuum container and an anti-coagulation vacuum container.

The device can be "charged" by sliding the second element 60 onto the first element 58 in a position so that the corresponding retainers, detents or snap-lock fittings 62 on the element 58 and 60 retain second element 60 in place. The insertion needle 28A may then be inserted into the umbilical cord or body. Valves 14 may then be controlled to couple the vacuum containers 18 to the insertion needle 28A as desired.

In the valve housing 12A shown in FIGS. 6 and 7, central chamber 20, intake chamber 22 and exhaust chambers 24 define tubular-shape exterior facings on the exterior surface of the housing 12A, while the remainder of the housing is substantially planar, the plane extending substantially through the axes of the chambers. The piece may be formed of plastic material and injection molded or otherwise easily formed or molded as desired, and it may fit neatly to enclosure 56 as shown.

The valves 14 are similar in structure and operation to those shown in FIGS. 1 and 2. In particular, left valve 14A may be pushed into housing 12A in order to connect injection needle 38A and exhaust needle 28B via first port 34, hollow portion 32 and second port 36 of valve shaft 30. Right valve 14B may be similarly positioned when and as desired, either serially or simultaneously with positioning of left valve 14A. Central chamber 20 may contain one or more detents or constricting rings to limit travel of valves 14 in order to reduce the possibility of their being retracted from the housing 12A inadvertently, and thus to reduce the possibility of inadvertent blood spillage. Additionally, a spring or other biasing means may be inserted in central chamber 20 between valves 14 in order to cause them to be positioned so as to close off the vacuum containers and injection needle 38A unless the user is actually pushing one or both of the valves.

The foregoing is provided for purposes of explanation and illustration. Modifications and enhancements to the embodiments described above may be made without departing from the scope or spirit of the invention.

What is claimed is:

1. A body fluid extraction device, comprising:
   (a) a housing containing an intake chamber, two exhaust chambers and a central chamber connecting the intake and exhaust chambers;
   (b) for each of the intake and exhaust chambers, an accommodation on the outer surface of the housing communicating with the chamber to which a hollow hypodermic needle may be connected; and
   (c) a pair of valves, each of which includes a shaft that slides in the central chamber and which includes:
      (i) a hollow portion;
      (ii) a first port located at a first location on the shaft and a second port located at a second location on the shaft, which ports communicate with each other through the hollow portions of the shaft, and which locations are positioned on the shaft so that they allow the intake chamber to communicate with an exhaust chamber associated with the valve when the valve is in the open position; and
      (iii) a pair of O rings positioned on the shaft between the first and second openings to form a closed space between the housing and the shaft, which closed space communicates with the associated exhaust chamber when the valve is in the closed position in order to disconnect the intake chamber from the exhaust chamber.

2. A body fluid extraction device, comprising:
   (a) a housing containing an intake chamber, two exhaust chambers and a central chamber which allows the intake and exhaust chambers to communicate;
   (b) for each of the intake and exhaust chambers, an accommodation formed on the housing for connection to a hollow hypodermic needle;
   (c) a hollow hypodermic needle connected to each accommodation in a fluid-tight relationship;
   (d) a vacuum container corresponding to each needle that is connected to an exhaust chamber;
   (e) a pair of valves, each of which includes a shaft which slides in the central chamber and which includes:
      (i) a hollow portion;
      (ii) a first port located at a first location on the shaft and a second port located at a second location on the shaft, which ports communicate with each other through the hollow portion of the shaft, and which locations are positioned on the shaft so that they allow the intake chamber to communicate with an exhaust chamber associated with the valve when the valve is in the open position; and
      (iii) a pair of O rings positioned on the shaft between the first and second openings to form a closed space between the housing and the shaft, which closed space communicates with the associated exhaust chamber when the valve is in the closed position in order to disconnect the intake chamber from the exhaust chamber;
   (f) A vacuum container enclosure, which comprises:
      (i) a first element which is connected to the housing and which encloses the needles that are connected to the exhaust chambers; and
      (ii) a second element which contains the lower portions of the vacuum containers, which connects to the first element in a sliding relationship and which is adapted to be slid toward the first element to force the needles into the vacuum containers.

3. A device according to claim 2 in which, for each valve shaft, the first port is located at the end of the shaft.

4. A device according to claim 2 in which at least one element of the vacuum container enclosure contains a detent to hold the elements together when the needles have been forced into the vacuum containers.

5. A device according to claim 2 further comprising a third O ring located so as to form a seal between the exhaust chamber and the exterior of the housing.

6. A device according to claim 2 in which the accommodations are fittings adapted to receive the needles.

7. A body fluid extraction device, comprising:
   (a) a housing containing an intake chamber and two exhaust chambers;
   (b) first connection means communication with the intake chamber for connecting a hollow hypodermic needle to that chamber;
   (c) valve means disposed intermediate the intake chamber and the exhaust chambers, which valve means may be positioned selectively to allow the intake chamber to communicate with each exhaust chamber, and to preclude the intake chamber from communicating with each exhaust chamber; and
   (d) second connection means communicating with each exhaust chamber for connecting a vacuum container in a fluid-tight relationship;
   (e) in which the valve means comprises a pair of valves, each of which includes a shaft which slides in the central chamber and which includes:
      (i) a hollow portion;
      (ii) a first port located at a first location on the shaft and a second port located at a second location on the shaft, which ports communicate with each other through the hollow portion of the shaft, and which locations are positioned on the shaft so that they allow the intake chamber to communicate with an exhaust chamber associated with the valve when the valve is in the open position; and
      (iii) a pair of O rings positioned on the shaft between the first and second openings to form a closed space between the housing and the shaft, which closed space communicates with the associated exhaust chamber when the valve is in the closed position in order to disconnect the intake chamber from the associated exhaust chamber.

* * * * *

UNITED STATES PATENT AND TRADEMARK OFFICE
CERTIFICATE OF CORRECTION

PATENT NO. : 5,097,842
DATED : March 24, 1992
INVENTOR(S) : Gina B. Bonn It is certified that error appears in the above-identified patent and that said Letters Patent is hereby corrected as shown below:

Column 5, line 27, "portions" should be --portion--

Column 6, line 33, "communication" should be --communicating--

Signed and Sealed this

Tenth Day of August, 1993

Attest:

MICHAEL K. KIRK

*Attesting Officer*   Acting Commissioner of Patents and Trademarks